(12) United States Patent
Parks et al.

(10) Patent No.: US 8,541,022 B2
(45) Date of Patent: Sep. 24, 2013

(54) METHOD OF TREATING BURNS USING AVERMECTIN COMPOUND

(75) Inventors: L. Dean Parks, Ocala, FL (US); Jeffrey D. Parks, Ormond Beach, FL (US)

(73) Assignee: Galderma S.A., Lausanne (CH)

( * ) Notice: Subject to any disclaimer, the term of this patent is extended or adjusted under 35 U.S.C. 154(b) by 1122 days.

(21) Appl. No.: 12/156,496

(22) Filed: Jun. 2, 2008

(65) Prior Publication Data

US 2009/0297589 A1    Dec. 3, 2009

(51) Int. Cl.
*A61F 13/00* (2006.01)
*A01N 43/04* (2006.01)

(52) U.S. Cl.
USPC .............................. 424/449; 514/28

(58) Field of Classification Search
None
See application file for complete search history.

(56) References Cited

U.S. PATENT DOCUMENTS 5,618,515 A * 4/1997 Singh et al. ................. 424/45
2002/0035076 A1   3/2002 Parks
2002/0156029 A1   10/2002 Parks
2004/0167084 A1   8/2004 Parks
2004/0202706 A1   10/2004 Koo et al.
2006/0194759 A1*  8/2006 Eidelson ..................... 514/54

FOREIGN PATENT DOCUMENTS

WO   WO 2006096913 A1 *  9/2006
WO   WO 2007054822        5/2007

OTHER PUBLICATIONS

Extended European Search Report (EESR) of counter-part European Patent Application No. EP 09 75 8700.

* cited by examiner

*Primary Examiner* — Lezah Roberts
*Assistant Examiner* — Nannette Holloman
(74) *Attorney, Agent, or Firm* — CUSPA Technology Law Associates; Yi Li

(57) ABSTRACT

A method of treating a superficial or partial thickness burn caused by heat, or by UV or laser radiation is disclosed. The method includes topically applying a topical composition containing an avermectin compound to an affected area immediately after a burn occurs. The method further includes cooling the affected area with ice or water prior to application of the topical composition. Additionally, the method includes topically applying a second topical composition containing fluocinonide and salicylic acid on the affected area to further enhance anti-inflammatory effect of the avermectin compound on the damaged skin.

12 Claims, No Drawings

# METHOD OF TREATING BURNS USING AVERMECTIN COMPOUND

FIELD OF THE INVENTION

The present invention relates to a method of treating a superficial or partial thickness burn caused by heat, or by UV or laser radiation using an avermectin compound.

BACKGROUND OF THE INVENTION

A burn can be an injury caused by heat, cold, electricity, chemicals, or radiation. Burns usually affect the skin, although other important areas of the body can also be injured. The severity of a burn of the skin depends on how deeply it has affected the tissue. There are three categories of burn: superficial, partial thickness and full thickness. These were previously referred to as first, second and third-degree burns.

Superficial burn is a burn that only affects epidermis, the surface of the skin. The skin appears red (erythema) and slightly swollen, and the burn is almost always painful. Partial thickness burn is a deeper burn, but it does not affect the whole depth of the skin. The epidermis is destroyed and the dermis, which is the layer of skin tissue below the epidermis, is also damaged to varying degrees. The skin appears deep red or purple, swollen and blistered, and the surface may have a weeping, wet appearance. The skin is extremely painful and hypersensitive, even to air movement. In the case of full thickness burn, the full depth of the skin is damaged and the skin appears dry and leathery. The skin may be pale or blackened. The full thickness burns are painless, because the nerve endings within the skin are also destroyed, although there is usually pain in the surrounding areas if they are affected by partial thickness burns.

Scalding is a specific type of burning that is caused by hot fluids (i.e. liquids or gases). Examples of common liquids that cause scalds are water and cooking oil. Steam is a common gas that causes scalds. Young children, with their delicate skin, can suffer a serious burn in a much shorter time of exposure than the average adult.

Sunburn is a burn to living tissue such as skin produced by overexposure to ultraviolet (UV) radiation. Sunburn of the skin occurs when incident UV radiation exceeds the existing protective capacity of melanin in the skin. A similar burn can be produced by overexposure to other sources of UV such as from tanning lamps, or occupationally, such as from welding arcs. Typically there is initial erythema, followed by varying degrees of pain, both proportional in severity to the duration and intensity of exposure. Other symptoms are edema, itching, red and/or peeling skin and rash. Sunburns may be superficial or partial thickness burns, or first- or second-degree burns.

In the recent years, another commonly seen burn caused by radiation is the burn caused by laser radiation used in laser therapy for cosmetic facial treatments and hair removal procedures. Laser facial resurfacing has been used to remove the upper layers of the skin on the face and it is an effective treatment for reducing mild scarring, or the effects of sun damage, such as fine wrinkles. In laser facial resurfacing procedure, a laser beam is radiated on the selected area of face to destroy epidermis in a carefully controlled manner, exposing the dermis. Then, at lower power, the laser heats the dermis, which stimulates the growth of new collagen fibers. Pulses of laser light can be used to treat skin lesions such as port wine stains and spider veins. These lasers can also be used to remove the color from tattoos and do not seriously damage the surrounding skin. Carbon dioxide or YAG lasers are often used for resurfacing procedures. The commonly seen side-effects of laser resurfacing include swollen skin that may ooze for the first 7-14 days after treatment and skin redness that may last for 6-12 weeks.

Laser hair removal is well established as an effective form of treatment for unwanted body hair, which is based on selective photothermolysis, or selective destruction of the follicular unit, resulting in significant hair reduction in treated areas. Adverse effects of laser hair removal are primarily related to epidermal damage by partial absorption of laser energy by the surrounding skin. This effect has been more pronounced in darker-skinned individuals whose increased skin melanin concentration places them at a higher risk of adverse effects. These adverse effects include blistering, hypo- or hyperpigmentation, scabbing, and rarely, permanent scarring.

Currently, superficial or partial thickness burns caused by heat is typically treated by flooding the affected areas with cold water until medical help, if necessary, is available. Large areas of partial thickness burns require medical treatment in hospitals, which typically involves applying dressings to protect the damaged skin. Superficial burns usually do not need dressings. Various over-the-counter ointments, creams and lotions are available for home treatment of minor burns, including sunburns. These topical compositions may include Aloe Vera, calamine, menthol, emu oil or other herbal ingredients. However, existing topical compositions have limited effects in reducing pain and preventing blistering caused by the burns. Even when they are applied immediately on the affected areas, or applied multiple times, they may not substantially reduce pains, typically they do not prevent blistering to occur.

It is known that the avermectin family of compounds is a series of very potent antiparasitic agents useful against a broad spectrum of endoparasites and ectoparasites in mammals and also having agricultural utilities against various nematode and insect parasites found in and on crops and in soil. Ivermectin is a member of the avermectin family; it has been used as an antiparasitic agent to treat various animal parasites and parasitic diseases since mid-1980's. It is commercially available for animal use as Cardomec (for felines), Zimecterin (for equines) and Ivomec (for bovines) by MERIAL Limited, Duluth, Ga. The medicine is available in tablets, paste, or chewables for heartworm prevention, topical solution for ear mite treatment, or as oral or injectable solution for other parasite problems.

Ivermectin is also commercially available from Merck & Co., Inc for human use as Stromectol® for eradication of threadworm *Strongyloides stercoralis*, and for eradication of *Onchocerca volvulus*. The medicine is available in tablets and is orally administered by the patients.

Magda et al., *Amer. J. Trop. Med. Hyg.* 53(6) 1995 pp. 652-653 describe a method of topical application of ivermectin to treat head lice. U.S. Pat. No. 5,952,372 (to McDaniel) discloses a method of treating a form of rosacea associated with the ectoparasite Demodex. U.S. Pat. Nos. 6,133,310, 6,433,006, 6,399,652, 6,399,651 and 6,319,945 (to Parks) disclose methods of treating acne rosacea, seborrheic dermatitis, acne vulgaris, transient acantholytic dermatitis, acne miliaris necrotica, acne varioliformis, perioral dermatitis, and acneiform eruptions by topically applying an avermectin compound, particularly ivermectin, to the affected areas.

However, avermectin compounds have not been used for treating burns caused by heat or by UV or laser radiation. It is also noted that none of the above described parasitic diseases and dermatological conditions are related to burns caused by heat or by UV or laser radiation.

Burns of the skin caused by heat, or by UV or laser radiation are common public problems. Therefore, there is a need for new and effective topical compositions for treating burns, particularly a topical composition which can be applied immediately after burning occurs to prevent blistering, and to reduce pain and other symptoms.

SUMMARY OF THE INVENTION

In one embodiment, the present invention is directed to a method of treating a superficial or partial thickness burn, which comprises topically applying a topical composition comprising an effective amount of an avermectin compound to an affected area of the skin of an individual immediately after a burn caused by heat, or by UV or laser radiation occurs. The avermectin compound comprises avermectins, avermectin derivatives, ivermectin, or ivermectin derivatives.

The method further comprises cooling the affected area with ice or water prior to applying the topical composition. The method may further comprise topically applying the topical composition to the affected area of the individual subsequently one or more times.

In a further embodiment, the present invention further comprises topically applying a second topical composition comprising fluocinonide and salicylic acid on the affected area to further enhance anti-inflammatory effect of the avermectin compound on the damaged skin.

The advantages of the present invention will become apparent from the following description in conjunction with exemplary embodiments of the invention.

DETAILED DESCRIPTION OF THE INVENTION

In one embodiment, the present invention provides a method of treating a superficial or partial thickness burn caused by heat, or by UV or laser radiation using an avermectin compound. The method comprises topically applying a topical composition comprising an effective amount of an avermectin compound to the affected areas of an individual immediately after a burn occurs.

The superficial burn and partial thickness burn are the burns traditionally referred to as the first-degree and second-degree burns, respectively. Herein, a burn caused by heat includes, but is not limited to, a burn caused by a skin contact with a hot surface such as stove, iron, and the like, with a hot liquid such as boiling water, heated oil or the like, with steam, and with hot air. A burn caused by UV radiation includes, but is not limited to, a burn caused by overexposure of the skin to ultraviolet (UV) radiation, including sun light and other sources of UV such as from tanning lamps and from welding arcs. A burn caused by laser radiation refers to a burn caused by a laser radiation used in dermatological or cosmetic skin treatments, such as laser facial resurfacing, or laser hair removal procedures.

Preferably, the topical composition comprising an avermectin compound is applied to the burned area as soon as possible. It has been found that in the situation of treating a burn caused by heat, when a thin coat of the topical composition is applied to the burned area immediately after the burn, pain relief is noted rapidly, and blister formation is attenuated or abated. Furthermore, the earlier the topical composition is applied, the better the treatment result is. The topical composition can also be applied again after the initial application one or more times, to reduce pain and blistering.

Therefore, it should be understood that the term "immediately after" means to topically apply the topical composition to the affected areas as quickly as possible. Considering various causes of the burns, topical application of the topical composition is preferably within 5 seconds to 45 minutes after a burn occurs, more preferably within 5 seconds to about 15 minutes, as further described below.

As can be appreciated, for burns caused by different reasons the time required for treatment can be different. In treating a burn caused by heat, the application of the topical composition is preferably within 5 seconds to about 5 minutes, more preferably, within 5 seconds to about 3 minutes after the burn occurs. In treating sunburns caused by overexposure to sun light, which typically takes a substantial period of time to occur, the topical application can be applied as soon as the sunburn is recognized or expected. In this situation, early application of the topical composition helps to achieve an optimal result, although the time is typically longer than that discussed above in treating burns caused by heat.

Moreover, the method can further include rubbing the affected area with ice cubes to cool and wet the skin, prior to applying the topical composition comprising an avermectin compound.

When treating a superficial or partial thickness burn caused by laser radiation used in laser therapy for cosmetic facial treatments and hair removal procedures, after the laser treatment, the anesthetic ointment is washed off first, then the topical composition containing avermectin compound is applied immediately to the area that has been treated. Typically, the hair removal procedure takes from about 5 minutes to about 30 minutes, depending on the area of treatment. The topical composition is applied from about 30 seconds to about 30 minutes, preferably from about 30 seconds to about 15 minutes, after the laser treatment is completed. The term "laser beam" refers to the laser beam used in laser therapy for cosmetic skin treatments and hair removal. Currently, 1064 nm wavelength is approved by FDA for permanent hair reduction.

As described above, an adverse effect commonly seen in laser hair removal is burns caused by partial absorption of laser energy by the surrounding skin, which can be a superficial or partial thickness burn. It has been found by the inventors that after the laser treatment procedure, topical application of the topical composition comprising an avermectin compound to the subject area reduces burns caused by the laser radiation, which is reflected by less pain, redness, swelling or blistering of surrounding skin.

The avermectin compounds for the purpose of the present invention include avermectin, avermectin derivatives, ivermectin, and ivermectin derivatives. The topical composition comprises an avermectin compound and a pharmaceutically acceptable carrier or a medium which is suitable for topical application to dermal tissues, as described further in detail hereinafter.

Preferably, ivermectin is used in the topical composition. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. The following molecular structure represents the avermectin series of compounds, which can be chemically converted to useful derivatives as discussed below.

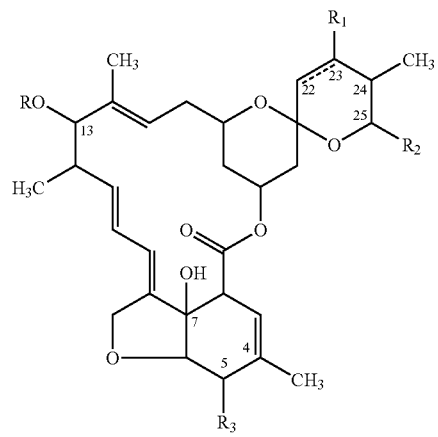

wherein the broken line indicates a single or double bond; $R_1$ is hydroxy and is present only when said broken line indicates a single bond; $R_2$ is isopropyl or sec-butyl; $R_3$ is methoxy or hydroxyl, and R is the 4'-(alpha-L-oleandrosyl)-alpha-L-oleandrose group of the structure:

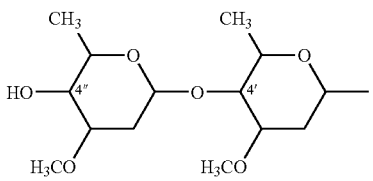

The avermectins, of which ivermectin, a chemically produced analog, is a member, are a series of compounds isolated from the fermentation broth of a C-076 producing strain of *Streptomyces avermitillis* and also chemically produced derivatives thereof. There are eight different but closely related compounds produced by *S. avermitillis*, designated as $A_{1a}, A_{1b}, A_{2a}, A_{2b}, B_{1a}, B_{1b}, B_{2a},$ and $B_{2b}$. The production of these compounds is described in U.S. Pat. No. 4,310,519. The preparation of ivermectin is disclosed in U.S. Pat. No. 4,199,569. The disclosures of each of the foregoing patents are incorporated herein by reference in their entirety.

Some of the avermectins contain a 22,23-double bond. This may be selectively reduced to prepare the ivermectin compounds. In addition, the avermectins possess a disaccharide moiety at the 13-position consisting of the alpha-L-oleandrosyl-alpha-L-oleandrosyl group. One or both of these saccharide groups may be removed as described in U.S. Pat. No. 4,206,205, and the produced aglycone derivatives have a hydroxy group at the 13-position. This group may be removed to form the 13-deoxy compound as described in U.S. Pat. Nos. 4,171,314 and 4,173,571; the latter patent also describes the 13-halo derivatives. The avermectin compounds and derivatives have several hydroxy groups which may be acylated as described in U.S. Pat. No. 4,201,861. U.S. Pat. No. 5,055,454 describes invert position 13 of avermectin from a normal alpha stereochemistry to the epimeric 13-beta stereochemistry. U.S. Pat. No. 5,077,308 describes avermectin aglycone derivatives which incorporate a ketal at position 13. U.S. Pat. No. 5,162,363 describes avermectin derivatives where the 23-position ring carbon atom is replaced with sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All aforementioned patents are incorporated herein by reference in their entirety.

All avermectin compounds mentioned above share the spectrum of anti-parasitic biological activity of ivermectin, varying only in degree. It is expected that they also share the activity spectrum of ivermectin suitable for the purpose of the present invention.

In a preferred embodiment, ivermectin is used. The concentration of ivermectin in the topical composition for the purpose of the present invention can be in a range from about 0.01% to about 10% weight by weight (w/w), preferably from about 0.03% to about 5% (w/w), and more preferably from about 0.05% to about 2% (w/w). It has been found that the topical composition containing ivermectin at a concentration as low as 0.075% is effective, as illustrated in the examples hereinafter, in treating superficial or partial thickness burn caused by heat, or by UV or laser radiation. Such a low effective concentration is advantageous because it reduces risks of side effects and the possibility of triggering body's autoimmune responses.

The topical composition can be in various forms, including, but not limited to, emulsion, lotion, cream, gel, ointment, spray, and foam. The topical composition can also be integrated into topic dressing, medicated tape, or dermal patch. The topic dressing or medicated tape can be used for a longer period of time. Furthermore, the topical composition can also be in the form of suspensions of microspheres or nanospheres, lipid or polymeric vesicles, or polymeric patches or hydrogels for controlled release, which is more suitable after the initial application.

Pharmaceutically acceptable carriers or media suitable for topical application on human skin are well known to those skilled in the art. In one embodiment, the topical composition is in a form of lotion or cream having substantially neutral pH from 6 to 7 and including one or more moisturizing agents. "Moisturizing agent," as used herein, includes any agent that facilitates hydration of the skin by inhibiting or preventing loss of water from the skin, absorbs water from the atmosphere and hydrates the skin, or enhances the skin's own ability to absorb water directly from the atmosphere, or a combination thereof. Without wishing to be bound by theory it is believed that the moisturizing agent also improves the skin's ability to absorb the avermectin compound. Suitable moisturizing agents include, but are not limited to, hydrophobic agents, and hydrophilic agents, or combinations thereof. Moisturizing agent, when used, are typically present in an amount from about 0.01 to about 20 weight percent, preferably about 0.05 to about 10 weight percent of the composition. Various moisturizing agents are known and have been used commercially in facial, body and hand creams or lotions. Examples 1 and 2 provide exemplary topical composition comprising ivermectin in a moisturizing lotion.

In Example 2, a commercially available moisturizing lotion manufactured by Galderma Laboratories, Inc. under the trade name Cetaphil® moisturizing lotion is used as the medium for ivermectin. Cetaphil® moisturizing lotion contains purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, farnesol, benzyl alcohol, phenoxyethanol, acrylates/C10-30 alkyl acrylate crosspolymer, sodium hydroxide, and citric acid.

In another embodiment, the topical composition is in the form of emulsion. An emulsion suitable to use for the method of the present invention is described in US Patent Application Publication No. US 2006/0100165, which is herein incorporated by reference in its entirety. More specifically, the topical composition comprises ivermectin, one or more solvents and/or propenetrating agent for the active agent, an oily phase, one or more surfactants functioning as emulsifier, and water. The topical composition can further comprise one or more gelling agents.

Suitable solvent and/or propenetrating agent for ivermectin includes, but not limited to, propylene glycol, alcohols such as ethanol, isopropanol, butanol, N-methyl-2-pyrrolidone or DMSO, polysorbate 80, phenoxyethanol, and mixtures thereof.

The oily phase can comprise vegetable, mineral, animal or synthetic oils, silicone oils, or mixtures thereof. Suitable mineral oil includes, but not limited to, paraffin oils of various viscosities. Suitable vegetable oil includes, but not limited to, sweet almond oil, palm oil, soybean oil, sesame oil and sunflower oil. Suitable animal oil includes, but not limited to, lanolin, squalene, fish oil and mink oil. Suitable synthetic oil includes, but not limited to, esters, such as cetearyl isononanoate, diisopropyl adipate, isopropyl palmitate, or caprylic capric triglyceride. Suitable silicone oil includes, but not limited to, dimethicone and cyclomethicone. Other suitable substances for the oil phase include, but not limited to, fatty acids such as stearic acid, fatty alcohols such as stearyl alcohol, cetostearyl alcohol and cetyl alcohol, or derivatives thereof, waxes such as beeswax, carnauba wax or candelilla wax, and gums such as silicone gums.

Various commercial available surfactants can be used as the emulsifier in the topical composition. Suitable examples include glyceryl/polyethylene glycol 100 stearate, polyoxyethylenated fatty acid esters, polyoxyethylenated stearyl alcohol, sorbitan esters such as sorbitan oleate, sorbitan sesquioleate and sorbitan isostearate, and fatty alcohol ethers.

Suitable gelling agents includes, but not limited to, carboxyvinyl polymers (carbomers), cellulose derivatives such as hydroxypropylmethylcellulose and hydroxyethylcellulose; xanthan gums, aluminum/magnesium silicates, guar gums, polyacrylamides, or mixtures thereof.

In an exemplary embodiment, the topical composition comprises from about 0.1 to about 20% by weight, preferably from about 1 to about 10%, of the solvent and/or propenetrating agent; from about 3 to about 50%, preferably from about 6 to about 20% by weight, of the oil phase; from about 2 to about 12% by weight, preferably from about 2 to about 6%, of surfactant; from about 0.01 to about 5% by weight, preferably from about 0.1 to about 3%, of gelling agent; and from about 30 to about 95% by weight, preferably from about 60 to about 80%, of water. The method of preparing an emulsion is known to those skilled in the art. A suitable example is provided in US Patent Application Publication No. US 2006/0100165.

Examples 3 and 4 illustrate the effectiveness of the method of the present invention in treating superficial or partial thickness burns caused by heat or by UV radiation. Drastically different from existing topical medications that have been used for treating burns, it has been found unexpectedly that when the ivermectin lotion was applied on the burned areas immediately after the burn occurs, typically within 30 seconds to 5 minutes, pain relief was rapidly noted (in a few minutes), and blister formation was attenuated or abated.

Example 5 further illustrates an example of the method of the present invention in treating burns caused by laser radiation used in cosmetic treatment and laser hair removal.

Although the Applicant is not bound by any theoretical explanation as to why the composition and the method of the present invention are effective in treating superficial or partial thickness burns caused by heat, or by UV or laser radiation, presentation of certain theoretical understanding may be of value. As can be appreciated, in treating superficial or partial thickness burns it is important to consider the damages done to the skin, which include degeneration and coagulation of proteins and cellular structures of the epidermis and dermis, as well as thrombosis of blood vessels. In addition, there is a release of toxic mediators of inflammation, which further damages all layers of the skin and the subcutaneous tissue that contains blood and lymphatic vessels, nerves, and elastic fibers that connect the dermis to the underlying fasciae. Based on clinical observations by the inventors, it is believed that the efficacy of the topic composition and the method of the present invention is due in part to the anti-inflammatory property of ivermectin. It is believed that ivermectin is an effective anti-inflammatory agent, which blocks certain mediators of inflammation, therefore, diminishes various symptoms caused by inflammation after the burns. Moreover, in view of the effect of ivermectin on neural system, it may also have some direct effects on the neural receptors in the skin, which may contribute to the rapid pain relief observed clinically.

In a further embodiment, the method of the present invention further comprises applying a second topical composition comprising fluocinonide and salicylic acid on the affected area after applying the topical composition comprising the avermectin compound. Fluocinonide is a potent glucocorticoid steroid, currently used topically as anti-inflammatory agent for the treatment of skin disorders such as eczema. It relieves itching, redness, dryness, crusting, scaling, inflammation, and discomfort. Commercially, 0.1% fluocinonide ointment is available for treating dermatological conditions. Salicylic acid has antiseptic effects which reduce the possibility of infection and putrefaction (decomposition of proteins). Preferably, the second topical composition comprises from about 0.05% to about 0.5% of fluocinonide and from about 5% to about 15% of salicylic acid. A thin coat of the second topical composition further adds to the anti-inflammatory effect of ivermectin, and enhances the overall effects in treating the burns.

The topical composition containing ivermectin and the second topical composition comprising fluocinonide and salicylic acid can be sold as a kit wherein the compositions are packaged in containers. Instruction on how to use these topical compositions in treating burns in accordance with the present invention are included on or associated with the containers.

The following examples are illustrative of the invention and are in no way to be interpreted as limiting the scope of the invention, as defined in the claims. It will be understood that various other ingredients and proportions may be employed, in accordance with the proceeding disclosure. It is further noted that the method of the present invention has been described in treating burns of human skin, however, it can also be used for treating burns of other mammals.

EXAMPLE 1

A lotion containing an avermectin compound is prepared as follows.

Mix 0.10 g of ivermectin (manufactured by Merck & Co., Inc.) with 2 ml of propylene glycol to dissolve ivermectin. The solution is then mixed sufficiently with 100 mg of Dove sensitive Skin facial lotion (manufactured by Unilever United States, Inc. Englewood Cliffs, N.J.) to make an ivermectin lotion, wherein the concentration of ivermectin is 0.10% (w/w).

Other suitable composition can be made in accordance with Example 1 which include ivermectin in the following concentrations: 0.05%, 0.075%, 0.2%, 0.5%, 1%, and 3% (w/w).

EXAMPLE 2

An ivermectin lotion is prepared as follows.

Mix 0.04 g of Zimecterin (manufactured by MERIAL Limited, Duluth, Ga.) which contains 1.87% ivermectin, sufficiently with 100 mg of Cetaphil® moisturizing lotion (manufactured by Galderma Laboratories, Inc.) to form an ivermectin lotion. The ivermectin concentration in the formed lotion is 0.075% (w/w).

Other suitable compositions can be made in accordance with Example 2 which include ivermectin in the following concentrations: 0.05%, 0.1%, 0.2%, 0.5%, 1%, and 3% (w/w)

with Cetaphil® moisturizing lotion as a medium. Other compatible commercial available lotions or creams can also be used as a medium or carrier.

EXAMPLE 3

Operating with informed consent of individuals, individuals were treated with the topical composition and the method of the present invention for superficial or partial thickness burns caused by heat or by UV or laser radiation.

In one instance, a person's hands and wrists were burned by steam. Within one minute after the scalding occurred, the burned areas were rubbed with ice cubes first to cool and wet the affected areas, then a thin coat of the ivermectin lotion of Example 2 was put on the burned areas immediately. In about 5 to 10 minutes, a substantial pain relief was observed. No blister formed on the burned areas. No further treatment was given after the single application of the ivermectin lotion.

In another instance, a person's thumbs were burned by accidentally touching the surface of a stove. Within one minute after the burn occurred, the burned areas were rubbed with ice cubes first to cool and wet the affected areas, then a thin coat of the ivermectin lotion of Example 2 was put on the burned areas immediately. In less than 10 minutes, a substantial pain relief was observed. No blister formed on the burned areas. The ivermectin lotion was applied two more times subsequently.

EXAMPLE 4

A male was exposed to sunlight for more than two hours at a beach without using sunscreen protection. The person felt severe pain on the neck and shoulders with extreme redness at these areas. About 45 minutes after the exposure, the sunburned areas were rinsed with cold water to wet the affected areas, then a thin coat of the ivermectin lotion of Example 2 was put on the neck and shoulders. In about 15 minutes, a substantial relief of pain was observed. The ivermectin lotion was applied two more times in the next 24 hours. No blister formed and no skin peel occurred at the sunburned areas.

EXAMPLE 5

A male was treated with laser hair removal procedure to remove hairs around ears. The patient's face was first cleaned according to the regular procedure for laser hair removal, and a topical anesthetic ointment was applied on the area. Then, the laser hair removal procedure was performed. After completing hair removal, the anesthetic ointment was washed off from the treated area, and a thin coat of the ivermectin lotion of Example 2 was applied on the treated areas. No further application of the topical composition was given afterwards. Follow up after the procedure showed that the patient had minimum erythema and swelling at the treated area, and no blister was formed.

In the above described informal trials, no adverse side effects or contra-indications were observed among the patients. The patients had no complaints of skin irritation originating from the treatment. There was no report of increasing skin sensitivity.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

What is claimed is:

1. A method for reducing pain and blistering caused by a superficial or partial thickness burn, comprising topically applying a topical composition comprising an effective amount of an avermectin compound to an affected area of the skin of an individual immediately after a burn caused by heat, or by UV or laser radiation occurs, thereby reducing said pain and blistering.

2. The method of claim 1, wherein said topically applying said topical composition is within 5 seconds to 45 minutes after said burn occurs.

3. The method of claim 2, wherein said topically applying said topical composition is within 5 seconds to 15 minutes after said burn occurs.

4. The method of claim 2 further comprising cooling said affected area with ice or water prior to said applying said topical composition.

5. The method of claim 2 further comprising topically applying said topical composition to said affected area of said individual subsequently one or more times.

6. The method of claim 2 further comprising topically applying a second topical composition comprising fluocinonide and salicylic acid on said affected area.

7. The method of claim 1, wherein said topical composition comprises an effective amount of said avermectin compound and a pharmaceutically acceptable carrier.

8. The method of claim 7, wherein said avermectin compound comprises avermectins, avermectin derivatives, ivermectin, or ivermectin derivatives.

9. The method of claim 8, wherein said avermectin compound is ivermectin in a concentration greater than 0.01% (w/w) in said topical composition.

10. The method of claim 8, wherein said ivermectin is in a concentration range from about 0.03% to about 5.0% (w/w).

11. The method of claim 7, wherein said topical composition is in a form of emulsion, gel, lotion, cream, or spray.

12. The method of claim 7, wherein said topical composition is integrated in a topical dressing, medicated tape, or dermal patch.

* * * * *